United States Patent [19]

Whistler

[11] Patent Number: 5,726,161
[45] Date of Patent: *Mar. 10, 1998

[54] POROUS PARTICLE AGGREGATE AND METHOD THEREFOR

[75] Inventor: Roy L. Whistler, West Lafayette, Ind.

[73] Assignee: Fuisz Technologies Ltd., Chantilly, Va.

[*] Notice: The term of this patent shall not extend beyond the expiration date of Pat. No. 5,486,507.

[21] Appl. No.: 416,741

[22] PCT Filed: Jan. 17, 1995

[86] PCT No.: PCT/US95/00707

§ 371 Date: Jul. 12, 1996

§ 102(e) Date: Jul. 12, 1996

[87] PCT Pub. No.: WO95/19376

PCT Pub. Date: Jul. 20, 1995

Related U.S. Application Data

[63] Continuation-in-part of Ser. No. 182,442, Jan. 14, 1994, Pat. No. 5,486,507.

[51] Int. Cl.⁶ .................. A61K 31/715; A01N 43/04; C08B 30/00; C07H 1/00

[52] U.S. Cl. ............... 514/54; 514/57; 514/60; 536/56; 536/102; 536/103; 536/114; 536/123.1; 536/124

[58] Field of Search ................... 536/102, 103, 536/56, 114, 123.1, 124; 514/54, 60, 57; 530/350

[56] References Cited

U.S. PATENT DOCUMENTS 5,464,632  11/1995  Cousin et al. .................. 424/465
5,486,507   1/1996  Whistler ........................... 514/54

Primary Examiner—John Kight
Assistant Examiner—Everett White
Attorney, Agent, or Firm—Sandra M. Nolan

[57] ABSTRACT

The invention deals with porous aggregates and a process for making same. The aggregates generally comprise discrete particles which are bound together, the aggregates having intra-aggregate volumes which may contain drug substances or other functional substances.

6 Claims, No Drawings

POROUS PARTICLE AGGREGATE AND METHOD THEREFOR

This application is a continuation-in-part application of U.S. Pat. No. 08/182,442 filed Jan. 14, 1994, now U.S. Pat. No. 5,486,507.

BACKGROUND AND SUMMARY OF THE INVENTION

This invention relates to particulate carriers for functional substances. More particularly, this invention is directed to particle aggregates having high porosity and a large intra-aggregate reticulate volume for containment of functional substances. The present aggregate compositions are economically manufactured to have predetermined release characteristics and other desired physical properties.

There has been a significant research and development effort directed to the definition and manufacture of carriers for functional substances for a wide variety of commercial applications. Ideal carrier compositions are those that inherently exhibit high capacity for carrying/containment of functional substances, those which work to enhance or prolong the functionality of the contained or carried substance, and those which can be economically manufactured to meet the unique specifications required for each targeted application. Such are the characteristics of the composition of the present invention.

In accordance with this invention, there is provided a versatile, low cost porous composition having a high void volume and thus a high capacity for containment for functional substances. The composition comprises free flowing aggregates of discrete particles, most preferably starch granules, bound together with a binder at their points of contact in the aggregate. The use of starch granules as the particle component of the present carrier composition provides surprisingly uniform spherical aggregates ranging in diameter from about 15 to about 150 microns, depending on the size distribution of the component starch granules. The surfaces of the aggregated particles cooperate to define an intraaggregate reticular volume for releasable containment of the functional substances. Advantageously the physical/chemical characteristics of the composition can be readily adjusted to meet the functional requirement of each targeted application by selection of the particle and binder components.

The particle aggregate compositions in accordance with this invention are prepared by forming a suspension of the particulate component in a solution of a binder and spray-drying the resulting suspension utilizing art-recognized spray drying equipment/technology. The particulate components can be pre-treated to promote their compatibility with the targeted functional substance and to impart other properties such as hardness and solubility characteristics appropriate for the contemplated carrier application. Further, the binder, typically a polymeric material exhibiting affinity for the particle component, can be selected according to its chemical and physical characteristics to optimize functionality of the particulate aggregates as a carrier in a targeted application. Thus the binder component can be selected with view of its solubility, its chemical reactivity, for example, its bioerodability or biodegradability, as appropriate to optimize functionality of the particle aggregates of the invention. Finally, the present aggregate compositions can be coated to provide additional functionality.

Functional substances can be easily introduced into the reticular volume of the present porous aggregates. The high intraaggregate reticular volume and high internal surface area of the present aggregate compositions allow high loading of functional substances. The loaded porous aggregate compositions of this invention are free flowing powders which facilitate handling and mixing of the functional substance in product formulations and further provides a matrix for sustained or prolonged release of the carried functional substance. Additionally, it is contemplated that the particle aggregates in accordance with this invention will exhibit functionality independent of their use as a carrier for functional substances. Thus, they may be used in prepared foods that require minute gritty character, either in mouth feel or in appearance. The particle aggregate composition in accordance with this invention has utility in the areas of food/nutrition, the preparation of topical creams and lotions, deodorant/antiperspirants, cosmetics, agricultural products, and products for human and veterinary medicine. For example, in a preferred embodiment, the aggregates of the invention may be included in a prepared food, such as a chewing gum. The present compositions can be designed to enhance and prolong the functional characteristics of contained functional compositions. Alternatively, the present composition can function to protect the contained functional substance from premature degradation. For example, orally administered pharmaceutical compositions can be formulated with/in the aggregate compositions, preferably the granular starch-based compositions of this invention, to provide an enteric formulation which functions to protect the active substance from the acid/digestive conditions of the stomach and thereafter release the active substance in the small intestine.

DETAILED DESCRIPTION OF THE INVENTION

In accordance with the present invention, there is provided a porous aggregate of discrete particles. The particle components of the present aggregates typically have an average particle size of about 1 to about 100 microns in their largest dimension. The particles are bound together with a binder, at least at their points of contact in the aggregate, so that the surfaces of the aggregated particles cooperate to define an intraaggregate reticular volume into which one can introduce functional substances. The contained substances are capable of being released from the aggregate over a period of time commensurate with the diffusion of the contained functional substance into the surrounding environment with or without the cooperation of disintegration of the aggregate due to solubilization or bioerosion/biodegradation of the binder or particulate components of the aggregate.

The present particle aggregate composition is prepared quite simply and economically by suspending the particles in a solution of a suitable binder and thereafter spray-drying the particulate suspension using art-recognized spray-drying methodology/equipment. Optionally the particle aggregate can be further processed by applying a polymer coating to the surface of the particulate aggregate after it is formed, either before or after a functional substance is introduced into the intraaggregate reticular volume. The coating process can be carried out using spray coater equipment such as that used in tablet manufacture or in art-recognized fluidized bed-type coating equipment.

The discrete particles utilized in preparing the present porous aggregates are preferably selected to have an average particle size of about 1 to about 100 microns, more preferably about 1 to about 75 microns, in their largest dimension. Exemplary of such particulate material useful in accordance with this invention are starch granules, particulate cellulosic materials such as micronized wood pulp or grain hulls, and particulate polymer materials such as those sold in the art as flattening agents for coating compositions, for example, pergopak® polymer particles sold by Martinswerk. Preferred particulate materials for use in accordance with this invention are granular starches, including native granular starches from various vegetable sources such as corn, barley, rice and wheat, which are known for their somewhat larger starch granules, and as well, from vegetable sources known to produce small starch granules such as amaranth, quinoa, dasheen, cow cockle, pigweed and Chinese taro. Small starch granules such as those from amaranth and the size classified small starch fraction of wheat starch are particularly preferred for use in accordance with this invention.

Granular starches, presumably due to their inherent spherical or spheroidal structure, form substantially spherical granular starch aggregates when used as the particulate component of the aggregate compositions of the present invention. Optionally the granular starch component of the preferred embodiments of present composition can comprise chemically modified granular starches including granular starches that have been rendered microporous by being subject to partial hydrolysis with acid or enzyme. Further, granular firmness and surface characteristics can be advantageously adjusted by pretreatment of the granules intended for use in the present particle aggregate compositions. Thus, for example, a greater degree of structural integrity and firmness can be introduced by pre-treating granular starch with an effective amount of a bifunctional starch-reactive chemical cross-linking agent. Any of a wide variety of art-recognized starch cross-linking agents, including those recognized as food-acceptable by the Food and Drug Administration, can be used. Suitable cross-linking agents include phosphates such as sodium trimetaphosphate, dicarboxylic acid derivatives, particularly $C_2$-$C_6$ dicarboxylic acids, including maleic and glutaric acid, phosphorous oxychloride, epichlorohydrin, and β, β-dichlorodiethylether Granular starches are rendered more resistance to mechanical damage, to swelling and to dissolution with increased degree of cross-linking.

Further the surface characteristics of the granular starches for use in preparation of the particle aggregates of the present invention, and thus the surface characteristics and absorptive capacity of the resultant aggregates, can be effected by other surface modification of the granular starch component. Thus granular starches intended for use in accordance with the present invention can be pre-treated with surface-modifying agents to enhance granule compatibility with functional substances targeted for use with the porous particle aggregate. If the substance to be introduced into the reticular volume of the particle aggregate composition has a predominant lipid character, the starch granules can be treated to render their surface more lipophilic. Thus, the granules can be surface treated with solutions of amphophilic polymers, or the surfaces of the granules can be chemically derivatized, for example, by reacting the granules with stearyl- or octyl-succinic acid anhydride. The granule surfaces are thereby rendered more lipophilic and more compatible with functional substances having a predominant lipid character. Surface characteristics of the granular starch component of the present compositions can also be modified for enhanced lipophilicity by pre-treatment with esterifying agents such as long chain fatty acids or derivatives thereof, or by etherification with long chain fatty halides. Treatment with acetic anhydride will also provide some lipophilic character to the granules, but a higher level of derivatization is required.

The porous particulate aggregates in accordance with this invention are prepared by spray-drying a slurry of particles in a solution of a binder component. The chemical nature of the binder is not critical, except to the extent that the binder should exhibit some threshold affinity for the surface of the discrete particles so that it can operate to bind the aggregated particulates together at least at their points of contact during the spray-drying process. Inherently, too, the binder component must have some threshold solubility in the liquid used to suspend the particle component prior to the spray drying operation. That liquid is typically water, however, other liquids such as $C_1$-$C_6$ alcohols, ethers and ketones may also be employed where the targeted functionality of the porous particle aggregate requires use of a binder not having the threshold solubility in water. Preferably, however, the porous particle aggregates in accordance with this invention are prepared by spray-drying aqueous suspensions of discrete particles, preferably starch granules, suspended in an aqueous solution of a binder.

There exists a wide variety of suitable binders that can be used in the formation of the present particle aggregates. They are, most typically, polymer compositions exhibiting the requisite degree of solubility in the liquid carrier for the particle suspension spray dried to form the porous aggregates. The polymer materials can be water soluble, water insoluble, biodegradable/bioerodable, not biodegradable, natural, synthetic, or semisynthetic —the binder to be selected for any particular application being dependent on the desired functionality, chemical/physical stability and release characteristics of the targeted aggregate in accordance with this invention. Preferred binders for use in accordance with this invention are biodegradable polymers such as polysaccharides including gums such as guar and locust bean gums, pectins, agar, alginate, gelatin, dextrins, dextran and derivatized starches and cellulosic materials such as carboxymethyl cellulose, hydroxymethyl cellulose, hydroxypropyl cellulose, and the like, proteins, particularly proteins other than those endogenous to the starch granules used to form the aggregates, and polyesters. Polysaccharides are preferred binders for use in accordance with the present invention. The binder components can also be non-biodegradable, synthetic or semi-synthetic polymers, such as polyvinyl alcohol, poly-N-vinyl-2-pyrrolidone, and polymers or co-polymers of acrylic or methacrylic acid and amide derivatives thereof, including polyacrylamide.

In accordance with the method embodiment of the present invention, porous aggregates of discrete particles are prepared by spray-drying a suspension of such particles in a solution of a suitable binder utilizing conventional spray-drying equipment/conditions. One limitation on the spray drying process is the stability of the particle component. Specifically, when spray-drying granular starch suspensions in aqueous binder solutions, it is very much preferred that the temperature in the spray-drying operation is not so high as to effect gelatinization of the starch granules.

The binder component is typically functional at very low levels, most preferably about 0.1 to about 2% by weight of the solution/suspension. The particulate component usually constitutes between about 2 and about 20 weight percent of the suspension prepared for spray-drying in accordance with this invention to produce the present porous particle aggregates.

The porous particle aggregate composition in accordance with this invention exhibits physical and chemical characteristics dependent on the constituent discrete particles and the binder component. The aggregates range in size from about 10 microns to about 250 microns, more typically between about 15 and 150 microns, most typically between about 10 and about 50 microns. The size and shape of the present particle aggregates depend significantly on the shape and particle size distribution of the component discrete particles. Thus when the preferred particle component, starch granules, are utilized to form the present porous aggregates, the aggregates assume a remarkably uniform spherical shape with the individual granules being bound together with the binder components at their points of contact. The surfaces of the aggregated starch granules cooperate to define an intraaggregate reticular volume for releasable containment of a functional substance.

The size, shape and particle size distribution of the porous particulate aggregates prepared in accordance with this invention are also dependent on the conditions selected for the spray-drying operating. Conventional spray-drying parameters, however, used to form the preferred starch-granule-based aggregates in accordance with this invention, produce surprisingly uniform porous, spherical aggregates.

The porous particles aggregate composition of the present invention is advantageously utilized as a carrier for a wide range of functional substances. The term "functional substances" as used herein to describe the present invention refers to any compound or composition which inherently possesses biological or other functional activity and which exhibits such activity to achieve some useful result when applied or used in a manner adapted to take advantage of such activity. Exemplary of such substances which can be absorbed into the intraaggregate reticular volume of such aggregates in accordance with such invention are salad oils, flavors, insect repellants, insecticides, herbicides, perfumes, moisturizers, soaps, antiperspirants, waxes, body creams and lotions, fertilizers, minerals, vitamins, bacteriostats, and therapeutic drug substances.

Salad oils such as hydrogenated or partially hydrogenated vegetable oils are useful as functional substances in the present invention and include materials such as corn oil, canola oil, rapeseed oil, cottonseed oil, sesame oil, soybean oil, grapeseed oil, sunflower oil, safflower oil, olive oil, peanut oil and the like.

A large variety of flavors may be included as functional substances in the present invention. The term "flavors" as used herein includes natural and synthetic flavoring materials as well as sweeteners. An illustrative list of such agents includes volatile oils, synthetic flavor oils, flavoring aromatics, oils, liquids, oleoresins or extracts derived from plants, leaves, flowers, fruits, stems and combination thereof. A non-limiting representative list of examples includes citrus oils such as lemon, orange, grape, lime and grapefruit and fruit essences including apple, pear, peach, grape, strawberry, raspberry, cherry, plum, pineapple, apricot or other fruit flavors.

Other useful flavorings include aldehydes and esters such as benzaldehyde (cherry, almond), citral, i.e., alphacitral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanal (green fruit), and 2-dodecenal (citrus, mandarin), mixtures thereof and the like.

Useful sweeteners may be chosen from the following non-limiting list: glucose (corn syrup), dextrose, invert sugar, fructose, and mixtures thereof; saccharin and its various salts such as the sodium salt; dipeptide sweeteners such as aspartame; dihydrochalcone compounds, glycyrrhizin; *Stevia rebaudiana* (Stevioside); chloro derivatives of sucrose such as sucralose; sugar alcohols such as sorbitol, mannitol, xylitol, and the like. Also contemplated are hydrogenated starch hydrolysates and the synthetic sweetener 3,6-dihydro-6- methyl-1-1-1,2,3-oxathiazin-4-one-2,2-dioxide particularly the potassium salt (acesulfame-K), and sodium and calcium salts thereof. Other sweeteners may also be used.

Therapeutic drug substances which can be used as functional substances in the present invention are varied. A non-limiting list of such substances is as follows: antitussives, antihistamines, decongestants, alkaloids, mineral supplements, laxatives, vitamins, antacids, ion exchange resins, anti-cholesterolemics, anti-lipid agents, antiarrhythmics, antipyretics, analgesics, appetite suppressants, expectorants, anti- anxiety agents, anti-ulcer agents, anti-inflammatory substances, coronary dilators, cerebral dilators, peripheral vasodilators, anti-infectives, psychotropics, antimanics, stimulants, gastrointestinal agents, sedatives, antidiarrheal preparations, anti-anginal drugs, vasodialators, anti-hypertensive drugs, vasoconstrictors, migraine treatments, antibiotics, tranquilizers, anti-psychotics, antitumor drugs, anticoagulants, antithrombotic drugs, hypnotics, anti-emetics, anti-nauseants, anti-convulsants, neuromuscular drugs, hyper- and hypoglycemic agents, thyroid and anti-thyroid preparations, diuretics, antispasmodics, uterine relaxants, mineral and nutritional additives, antiobesity drugs, anabolic drugs, erythropoietic drugs, antiasthmatics, cough suppressants, mucolytics, anti-uricemic drugs and mixtures thereof.

Especially preferred active ingredients contemplated for use in the aforementioned enteric formulations of the present invention are antacids, $H_2$-antagonists, and analgesics. For example, antacid dosages can be prepared using the ingredients calcium carbonate alone or in combination with magnesium hydroxide, and/or aluminum hydroxide. Moreover, antacids can be used in combination with $H_2$-antagonists.

Analgesics include aspirin, acetaminophen, acetaminophen plus caffeine, and ibuprofen.

Such functional substances can be absorbed or otherwise introduced into the porous aggregates of the present invention either by spraying solutions of such substances onto the prepared aggregates, adding such substances to the particle slurries prior to the spray drying process, or by adding the aggregates to solutions of said substances wherein the solvent for such substances is selected so as not to prematurely dissolve or otherwise disrupt the aggregate binder component. The product aggregates containing functional substances within the reticular volume defined by the surfaces of the aggregated particles can be isolated in the process by utilizing art-recognized techniques such as filtration, centrification, air classification and drying. The degree of loading of functional substances into the porous aggregates can be controlled in part by adjusting the concentration of the functional substance in the solutions used to load the aggregate matrices. Higher concentrations of the loaded material can be achieved using more concentrated solutions of the substances and by repeating the loading procedure. Preferably the substances are introduced into the porous particulate aggregates either as a component of the spray dried slurry or suspension used to form the aggregates, or as in solution in an inert, relatively low boiling solvent, which can be removed by evaporation following loading of the aggregate matrix. A hydrophobic liquid, such as a flavor oil, can be loaded into the aggregate by simply allowing the oil to soak into the porous aggregate.

The release characteristics and other physical properties of the particulate aggregates in accordance with this invention can be further modified by coating the aggregates following their preparation with a solution of a coating composition which may be the same as or different from the binder/polymer. The coating operation is preferably carried out after the loading of the aggregates with the desired functional substance. The coating operation can be accomplished simply by spraying the porous particulate aggregate composition with a dilute solution of a coating composition which may be the same as or different from that used as the binder component of the aggregate composition. The coating operation can be conducted in spray coater type equipment such as that used for conventional tablet coating operations or in conventional fluidized bed-type coating pan equipment. Other such conventional operations include pan coating processes, spray coating processes, and drum coating processes. The coating composition utilized in the optional aggregate coating operation can be selected to optimize the targeted functionality of the aggregate carrier composition. Suitable coating compositions include any of those mentioned above as binder components and as well other art-recognized coating compositions utilized in conventional tablet coating applications.

Other such art-recognized coating compositions include coating materials such as film forming materials. Film forming materials such as fats, natural resins, natural polymeric materials, and synthetic polymeric materials are included as coating materials according to the invention. A non-limiting list of types of suitable coating materials includes: molten coating materials such as partially hydrogenated cottonseed oil, partially hydrogenated palm oil, partially hydrogenated soybean oil, partially hydrogenated castor oil, beeswax, carnauba wax, polyethylene glycol, paraffin, long chain alcohol esters, gelatin/wax materials, and gelatin/fat materials; aqueous polymeric dispersion polymers such as L30D (copoly methacrylic acid/ethylacrylate), RS/RL30D (copoly ethylacrylate/methyl methacrylate/trimethylammonium ethyl methacrylate chloride), NE30D (copoly ethylacrylate/methyl methacrylate/ethyl cellulose), Sureloase (ethylcellulose), EC Aquateric (ethyl cellulose/cellulose acetate phthalate), Coateric (polyvinyl acetate), and Coateric (polyvinyl acetate phthalate-hydroxypropyl methyl cellulose acetate succinate); and solvent coating polymers such as methyl cellulose, hydroxypropyl methylcellulose, ethyl cellulose, cellulose acetate, cellulose triacetate, cellulose acetate butyrate, cellulose acetate phthalate, cellulose acetate trimellitate, carboxy methyl cellulose, hydroxypropyl methyl cellulose phthalate, methacrylic acid polymers and copolymers, and methacrylate polymers and copolymers.

The porous particle aggregates in accordance with this invention can be used, without added functional substances, as a bulking agent or to impart other desirable organoleptic characteristics such as mouth feel, in various prepared foods. Preferably, however, the present compositions are used as carrier and excipient for functional substances to enhance or prolong substance functionality. Thus, for example, the present composition can be utilized as a carrier for functional liquids, essentially converting them in form to free-flowing powders which can be used as a substitute for such functional substances in compositions to promote and/or prolong substance functionality. The carried or contained functional substances are released from the porous particulate aggregate, by simple diffusion, or upon mechanical compression or by chemical degradation or simple dissolution of the binder and/or particle components. Thus, for example, it has been found that granular starch aggregates in accordance with this invention utilizing a guar gum or carboxymethyl cellulose binder can be "loaded" with a flavor oil and used as a component of chewing gum to prolong flavor release.

The following Examples are presented to illustrate the present invention and should not in any way be construed as a limitation thereof.

EXAMPLE 1

Amaranth starch granules are slurried in a solution of about 0.5 to about 1% by weight of a commercial high viscosity guar gum to produce strong spherical aggregates. The spherical aggregates range from about 10 to about 30 microns in diameter.

EXAMPLE 2

Granular amaranth starch was suspended in a 0.1% guar gum solution and spray dried to produce spherical aggregates having a size range of about 10 to about 30 microns. The aggregates were dispersed in mint oil, centrifuged and thereafter washed with ethanol in a fritted glass funnel and dried to provide a mint oil loaded aggregate composition containing about 35% by weight mint oil. The mint oil loaded starch aggregate composition was then spray coated with a 0.5% solution of guar gum. The coated spheres were essentially without odor, but released mint oil and odor when they were rubbed on a glass plate with a metal spatula.

EXAMPLE 3

A slurry of rice starch in a 1% aqueous solution of locust bean gum is spray dried to produce porous spherical aggregates having a high intraaggregate reticular volume.

EXAMPLE 4

The small granular fraction of wheat starch obtained by size classification of native wheat starch is slurried in an aqueous medium containing medium viscosity methylhydroxypropyl cellulose and spray dried to produce substantially spherical aggregates of small wheat starch granules. The aggregates are dispersed in mint oil, centrifuged and thereafter washed with ethanol in a fritted glass funnel and dried to provide a mint oil loaded aggregate composition containing about 48% by weight mint oil. The mint oil loaded starch aggregate composition is then spray coated with a 0.5% solution of gelatin. The coated spheres are essentially without odor, but release mint oil and odor when they are rubbed on a glass plate with a metal spatula.

EXAMPLE 5

A suspension of 10 grams of a micronized wood pulp having an average particle size of about 5 to about 15 microns in 150 ml of ethanol containing 1.5% by weight of poly-N-vinyl-pyrrolidone is spray-dried in a conventional spray dryer to produce porous aggregates. The aggregate composition is dispersed in an aqueous solution of a pesticide, filtered and dried to provide a pesticide loaded particle aggregate composition in accordance with this invention.

EXAMPLE 6

Rice starch is slurried in 0.1% guar gum solution and spray dried to produce a free-flowing powder comprising spherical aggregates about 30 microns in diameter. The aggregates are non-hygroscopic and hold their spherical shape under normal processing. The disintegration of the rice starch aggregates in water occurs over a period of time during which the inter-granular binding gum is dissolved to allow disintegration of the spheres.

EXAMPLE 7

Commercial corn starch is dispersed into a 0.1% by weight solution of carboxymethyl cellulose and spray dried to yield aggregates of granular corn starch in accordance with this invention.

EXAMPLE 8

Rice starch is suspended for 5 minutes in a 0.2% solution of 20 DE (dextrose equivalent) starch dextrin and spray-dried at 120° C., spray nozzle setting to produce well defined spherical aggregates of rice starch.

EXAMPLE 9

Amaranth starch granules are suspended in a 0.1% sodium alginate solution and spray dried to form an alginate-bonded granular aggregate. The product is sprayed or briefly washed with a 1% calcium chloride solution to convert the sodium alginate binder to water insoluble calcium alginate. The resulting spheres exhibit enhanced stability under aqueous conditions up to temperatures near the gelatinization temperature of the starch component. The spheres are spray coated with a 1% sodium alginate solution and thereafter sprayed with calcium chloride solution to increase physical stability and water resistance. Mint oil filled/calcium alginate coated spheres are stabilized to oil leakage from the aggregate composition.

EXAMPLE 10

Aggregates of amaranth and wheat starch formed with either a carboxymethyl cellulose or locust bean gum binder are incorporated at 2% by weight into an ice cream composition prepared with but 50% of the normal fat content, without compromise of taste and mouth feel.

EXAMPLE 11

The small granular fraction of wheat starch is slurried in an aqueous solution of 0.1% gelatin and spray dried to produce porous, substantially spherical aggregates. The aggregate composition is slurried in an alcoholic solution of an orally effective antibiotic, then filtered and dried. The dried aggregates are coated in a fluidized bed coating machine with a 0.5% solution of ethyl cellulose of the type used for tablet coating. The coated aggregates are filled into capsules for oral administration.

I claim:

1. A composition comprising substantially spherical porous aggregates of starch granules bound together with a binder at least at their points of contact in said aggregates, the surface of said aggregated starch granules cooperating to define an intraaggregate reticulate volume which releasably contains therein a functional substance selected from the group consisting of: salad oils, flavors, insect repellants, insecticides, herbicides, perfumes, moisturizers, soaps, antiperspirants, waxes, body creams and lotions, fertilizers, minerals, vitamins, bacteriostats and therapeutic drug substances.

2. The composition of claim 1 wherein said functional substance comprises a therapeutic drug substance.

3. The composition of claim 1 wherein said composition is a prepared food.

4. The composition of claim 3 wherein the prepared food is chewing gum.

5. A composition comprising an aggregate of discrete particles, said particles having an average particle size of about 1 to about 100 microns in their largest dimension, said particles bound together with a binder not endogenous to the particles at least at their points of contact in said aggregate, the surfaces of said aggregated particles cooperating to define an intraaggregate reticular volume releasably containing a therapeutic drug substance.

6. A method for preparing porous aggregates of discrete particles having an average particle size of about 1 to about 100 microns in their largest dimension, said aggregated particles bound together to form reticulate volumes in said porous aggregates with a binder not endogenous to the discrete particles at least at their points of contact in said aggregate, said method comprising the steps of:

(1) forming a suspension of said particles in a solution of the binder and spray-drying said suspension, and (2) introducing a therapeutic drug substance into the reticulate volumes of the aggregates.

\* \* \* \* \*